United States Patent
Wrobel

(10) Patent No.: US 12,318,242 B2
(45) Date of Patent: Jun. 3, 2025

(54) METHOD AND DEVICE FOR A NON-INVASIVE DETERMINATION AND/OR MONITORING OF INTRACRANIAL COMPLIANCE

(71) Applicant: SONOVUM GMBH, Leipzig (DE)

(72) Inventor: Miroslaw Wrobel, Leipzig (DE)

(73) Assignee: SONOVUM GMBH, Leipzig (DE)

( * ) Notice: Subject to any disclaimer, the term of this patent is extended or adjusted under 35 U.S.C. 154(b) by 0 days.

(21) Appl. No.: 17/599,182

(22) PCT Filed: Mar. 27, 2020

(86) PCT No.: PCT/EP2020/058708
§ 371 (c)(1),
(2) Date: Sep. 28, 2021

(87) PCT Pub. No.: WO2020/201083
PCT Pub. Date: Oct. 8, 2020

(65) Prior Publication Data
US 2022/0183656 A1 Jun. 16, 2022

(30) Foreign Application Priority Data
Apr. 3, 2019 (EP) .................................... 19166970

(51) Int. Cl.
*A61B 8/06* (2006.01)
*A61B 8/00* (2006.01)
(Continued)

(52) U.S. Cl.
CPC .............. *A61B 8/06* (2013.01); *A61B 8/0808* (2013.01); *A61B 8/15* (2013.01); *A61B 8/4209* (2013.01)

(58) Field of Classification Search
CPC ........... A61B 8/06; A61B 8/0808; A61B 8/15; A61B 8/4209
See application file for complete search history.

(56) References Cited

U.S. PATENT DOCUMENTS 9,826,934 B2 * 11/2017 Oliveira ............... A61B 5/4094
2002/0095087 A1 7/2002 Mourad et al.
(Continued)

FOREIGN PATENT DOCUMENTS

| RU | 2163090 C1 | 2/2001 |
|---|---|---|
| RU | 2570545 C1 | 12/2015 |
| WO | 2017118964 A1 | 7/2017 |

OTHER PUBLICATIONS

Ragauskas, A., et al. "Non-invasive assessment of intracranial biomechanics of the human brain," Ultragarsas (Ultrasound) Journal. vol. 63(1), 2008. p. 38-46 (Year: 2008).*
(Continued)

*Primary Examiner* — Sean A Frith
(74) *Attorney, Agent, or Firm* — Quarles & Brady LLP

(57) ABSTRACT

A method for a noninvasive determination and/or monitoring of the intracranial compliance of a biological material includes performing an acoustic spectroscopy of a human or an animal skull; comparing the acoustic transmitting signals with the corresponding acoustic receiving signals, and determining a function in n-dimensions, which is characteristic for the biological material; determining the expansion of the biological material, the linear expansion and/or volume expansion of the biological material being measured, and determining the intracranial compliance of the biological material based on the comparisons.

13 Claims, 5 Drawing Sheets

Figure 1:
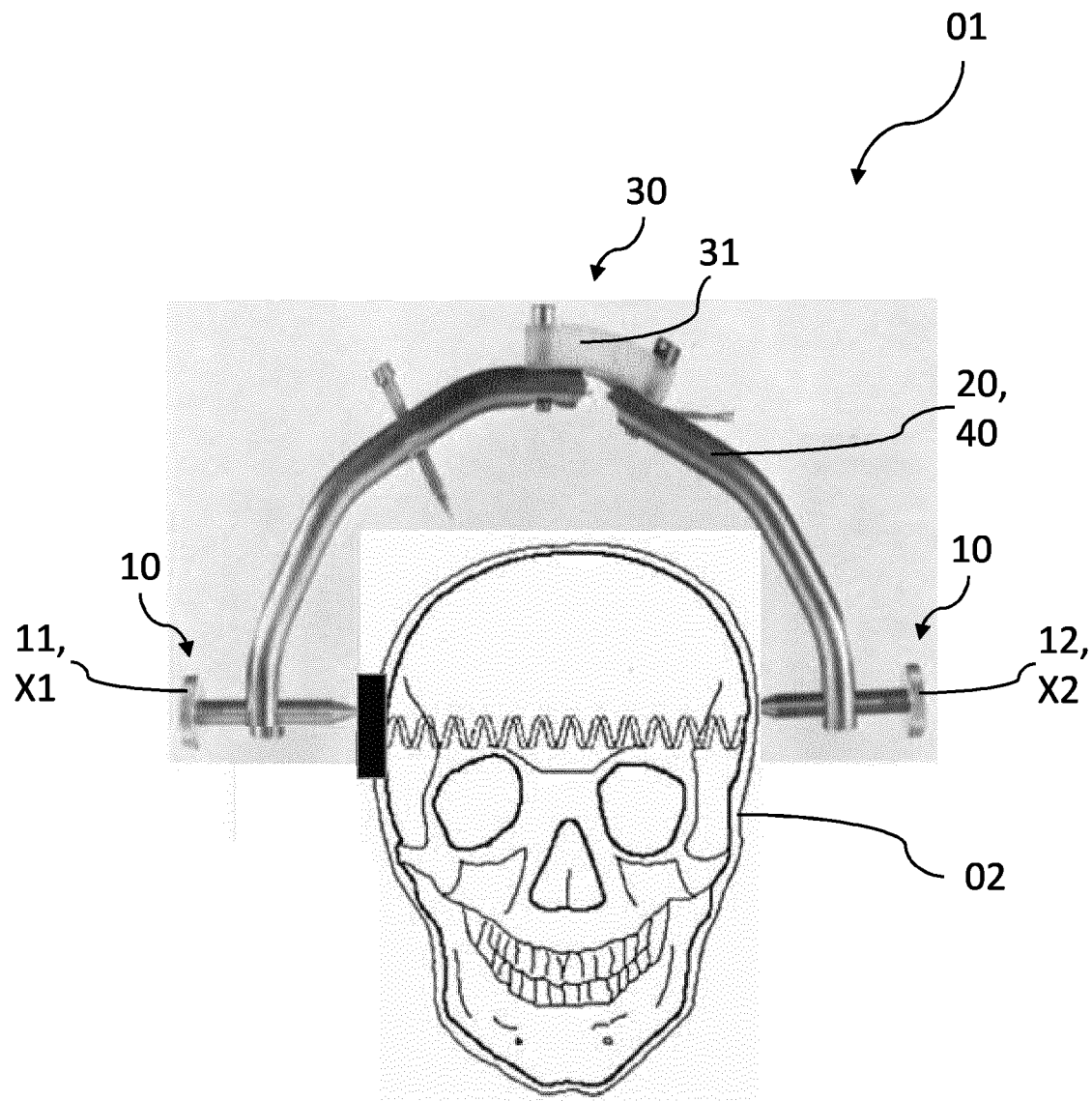

(51) Int. Cl.
*A61B 8/08* (2006.01)
*A61B 8/15* (2006.01)

(56) References Cited

U.S. PATENT DOCUMENTS

| | | | |
|---|---|---|---|
| 2002/0161304 | A1 | 10/2002 | Eide |
| 2003/0060711 | A1* | 3/2003 | Michaeli ............ A61B 8/0808 600/451 |
| 2006/0100530 | A1 | 5/2006 | Kliot et al. |
| 2009/0198137 | A1* | 8/2009 | Ragauskas ........... A61B 8/0808 600/449 |
| 2013/0197390 | A1 | 8/2013 | Weinberg et al. |
| 2015/0313577 | A1* | 11/2015 | Duric ................. A61B 8/5207 600/438 |
| 2016/0278736 | A1 | 9/2016 | Hamilton et al. |
| 2018/0214117 | A1 | 8/2018 | Oura |
| 2019/0282108 | A1* | 9/2019 | Beach ................... A61B 5/257 |

OTHER PUBLICATIONS

Ganpule, S., et al. "Effect of bulk modulus on deformation of the brain under rotational accelerations," Shock Waves. vol. 28(1), 2018. p. 127-139 (Year: 2018).*

Hargens, Noninvasive Intracranial Volume and Pressure Measurements Using Ultrasound (Head and Spinal), Annual Report Prepared for U.S. Army Medical and Research and Materiel Command, Mar. 1999, 18 pages.

Heifetz et al., Detection of Skull Expansion with Increased Intracranial Pressure, Journal of Neurosurgery, 1981, 55:811-812.

Petkus et al., Investigation of Intracranial Media Ultrasonic Monitoring Model, Ultrasonics, 2002, 40:829-833.

Raboel et al., Intracranial Pressure Monitoring: Invasive Versus Non-Invasive Methods—A Review, Critical Care Research and Practice, 2012, vol. 2012, Article ID 950393, 14 pages.

Ragauskas et al., Non-Invasive Assessment of Intracranial Biomechanics of the Human Brain, Ultragarsas/Ultrasound, 2008, 63(1):38-46.

Steinbach et al., Intracranial Pressure Dynamics Assessed by Noninvasive Ultrasound During 30 Days of Bed Rest, Aviation, Space, and Environmental Medicine, 2005, 76(2):85-90.

Ueno et al., Pulsed Phase Lock Loop Device for Monitoring Intracranial Pressure During Space Flight, Journal of Gravitational Physiology, 2003, 10(1):P-117-P-118.

Ueno et al., Noninvasive Assessment of Intracranial Pressure Waveforms by Using Pulsed Phase Lock Loop Technology, Journal of Neurosurgery, 2005, 103:361-367.

Wagshul et al., The Pulsating Brain: A Review of Experimental and Clinical Studies of Intracranial Pulsatility, Fluids and Barriers of the CNS, 2011, 8:5, pp. 1-23.

PCT International Search Report and Written Opinion, PCT/EP2020/058708, Jul. 24, 2020, 18 pages.

Japan Patent Office, Notice of Reasons for Refusal, Application No. 2021-560237, May 30, 2023, 5 pages.

Federal Service for Intellectual Property—Russia, Search Report, Application No. 2021130474, Mar. 29, 2023, 2 pages [No English Language Translation Available].

* cited by examiner 1a  1b  2  3  5  3  2  1b  1a
         4

US 12,318,242 B2

METHOD AND DEVICE FOR A NON-INVASIVE DETERMINATION AND/OR MONITORING OF INTRACRANIAL COMPLIANCE

This application is a national stage application of International Patent Application No. PCT/EP2020/058708 filed on Mar. 27, 2020, which claims priority to European Patent Application 19166970.4, filed on Apr. 1, 2019, which applications are hereby incorporated by reference in their entirety.

The disclosure relates to a method and a device for a noninvasive determination and/or monitoring of the intracranial compliance of a biological material according to the preamble of the independent claims.

The development of a change in intracranial pressure (ICP) in the human or animal skull significantly complicates numerous cerebral diseases and considerably influences mobility and mortality and further prognoses. For example, it has been found that 18% of patients with severe brain damages, such as after a traumatic brain injury and/or a stroke, have permanent functional damages, which require a long-term occupational and/or social rehabilitation. The extent of these damages is not only determined by the primary severity of the respective trauma, but is significantly influenced by secondary brain damages. As a result, a change in intracranial pressure which is not recognized in time and treated adequately can be of significant partheno-genetic importance. Thus, the measurement of the intracranial pressure is an important indicator for therapeutic decisions when treating patients with severe brain damages. It is therefore not surprising that the state of the art proposes a preferably continuous measurement of the intracranial pressure, which is not only therapeutically relevant, but also prognostically relevant.

Different methods and devices for measuring the intracranial pressure are known from the state of the art. However, until now, the intracranial pressure has been measured only by means of neurosurgically intracranially-implanted pressure probes, the measurement being carried out via an intraventricular or epidural pressure probe and allowing a continuous monitoring of the intracranial pressure, even over longer periods of time. However, it is disadvantageous that the methods and devices known from the state of the art are invasive and that they require a neurosurgical procedure, including the risk of infection associated therewith.

Thus, prior art has continuously attempted to develop noninvasive methods and devices for monitoring intracranial pressure. In this regard, reference is made to transcranial Duplex sonography (TCD), which allows a direct, noninvasive analysis of the cerebral hemodynamics in the major basal cerebral arteries. However, this method is disadvantageous in the sense that only approximate assertions regarding the intracranial pressure of the human or animal skull can be made. This is also disadvantageous in that transcranial Doppler sonography is difficult to carry out and thus must be performed by specially trained medical personnel.

Furthermore, other direct, noninvasive methods and/or devices for monitoring the intracranial pressure are known from the state of the art. In this regard, references include, but are not limited to, the following: "The pulsating brain: A review of experimental and clinical studies of intracranial pulsatility", "Pulsed Phase Lock Loop Device for Monitoring Intracranial Pressure During Space Flight", "Noninvasive assessment of intracranial pressure waveforms by using pulsed phase lock loop technology: Technical note", "Detection of skull expansion with increased intracranial pressure", "Investigation of intracranial media ultrasonic monitoring model", "Intracranial Pressure Dynamics Assessed by Noninvasive Ultrasound During 30 Days of Bed Rest", "Intracranial Pressure Monitoring: Invasive versus Non-Invasive Methods—A Review" and "Noninvasive Intracranial Volume and Pressure Measurements Using Ultrasound (Head and Spinal)". However, these methods and/or devices known from the state of the art are disadvantageous in the sense that it is not possible to exactly determine and/or monitor the intracranial pressure and the brain damages associated therewith.

Additionally, Arterial Duplex Ultrasound is known from the state of the art as a recognized diagnostic technology for monitoring the extracranial neck vessels, in particular the A. Carotis and the A. Vertebral. Thus, Arterial Duplex Ultrasound provides valuable information regarding calcifications and related blood turbulences and/or anemia/lack of blood. However, it has turned out to be a problem that the thickness of the skull and the related sound absorption prevents a similarly detailed imaging procedure for examination of the intracranial vessels. Thus, the imaging ultrasound technology is, on the one hand, an important and proven instrument for the diagnosis and therapy in the medical field, wherein these systems unfortunately only supply information on the internal structure of an object as a 2D or 3D image, but not on the composition of the object.

Thus, there is a high demand for a method and a device for a noninvasive determination and/or monitoring of the intracranial compliance of a biologic material, which ensures a simple, quick, reliable and adequately precise determination and/or monitoring of the state of the biological material, in order to recognize a change in intracranial pressure in time and/or to treat it adequately. Additionally, the method and the device should be suitable for an inexpensive production, should work reliably and should be suitable for a short-term or long-term determination and/or monitoring of the biological material. A further aspect is that the determination and/or monitoring of the intracranial compliance should be carried out such that it is insusceptible to errors, error-free, low-maintenance, low-noise, free of side effects and non-impairing for the respective patient. Thus, the object of the disclosure is to provide a method and a device for a noninvasive determination and/or monitoring of the intracranial compliance of a biological material, in order to overcome the difficulties mentioned above and especially in order to timely recognize a change in intracranial pressure and/or secondary brain damages.

This object is attained in a surprisingly simple but effective manner by a method for a noninvasive determination and/or monitoring of the intracranial compliance of a biological material and a corresponding device according to the teachings of the independent main claims.

According to the disclosure, a method for a noninvasive determination and/or monitoring of the intracranial compliance of a biological material is proposed, which comprises the following steps:

a) Performing an acoustic spectroscopy of the biological material, several acoustic transmitting signals of different frequencies and/or amplitudes being emitted into the biological material and corresponding reflected and/or transmitted acoustic receiving signals of different frequencies and/or amplitudes being received after having passed through the biological material, and the biological material being a human or an animal skull; and b) comparing the acoustic transmitting signals with the corresponding acoustic receiving signals, a function in n-dimensions, which is characteristic for the biological material, and the time-of-flight values being determined; and c) determining the expansion of the biological material, the linear expansion and/or the volume expansion of the biological material being measured, and, d) determining the intracranial compliance of the biological material based on the comparisons drawn in step b) and the measurement carried out in step c).

The fundamental concept of the method according to the disclosure is based on the fact that for an adequately precise detection and the associated adequate treatment of the changed intracranial pressure, it is sufficient to determine and/or monitor the intracranial compliance of the human or animal skull. In the course of this, it has been detected that, based on the acoustic spectroscopy of the human or animal skull, time-of-flight of the acoustic signal is measured and, simultaneously, its changes of the measuring section and the speed of sound. Based on this data, the intracranial compliance can be reliably determined in an adequate measuring range and can thus allow conclusions to be drawn regarding the intracranial pressure, the cerebral blood flow and/or a pathological condition, in particular by separating the measured values. This is based on the fact that within the scope of the present disclosure, it has been detected that the concept according to the disclosure, namely Acoustocerebrography (ACG), which pursues a different possible approach of sound application, can be applied to the biological material. It has thus been detected that the use of several frequencies shows the dispersive character of the brain tissue and allows a specific interpretation of the signal changes. Dispersion is an effect, in which the nonlinear, frequency-dependent compressive modulus of the medium leads to different propagation speeds for different sound frequencies. In nonlinear material, such as biological tissue and, in particular, human or animal brain tissue, an effect of the sound wave dispersion can be clearly observed and measured. It is an effect, in which the compressive modulus of the nonlinear frequency-depending medium leads to different propagation speeds for different sound frequencies. Since the properties of the compressive modulus depend on the specific features of the medium, such as composition, mixing concentration, dispersion and/or in some cases also the chemical composition, the pattern of the frequency-dependent propagation speeds can be used for identifying the medium. In other words, it can be seen from the following equations (Eqn. 1) and (Eqn. 2), that the propagation speed c(f) is a function of the frequency and/or the wavelength. It is dependent on the compressive modulus or modulus of elasticity $K_v$ for liquid mediums and on the compressive modulus $K_B$ for solid mediums.

$$c = \sqrt{\frac{K}{\rho}} = \sqrt{V * \frac{dp}{dV * \frac{m}{V}}} = V * \sqrt{\frac{dp}{dV * m}} \quad \text{(Eqn. 1)}$$

$$c_{ad}(f) = \sqrt{\frac{K(f)}{\rho * \beta_{ad}}} \quad \text{(Eqn. 2)}$$

It can be seen from the equations (Eqn. 1) and Eqn. 2) that the compressive modulus K can be split into the volume V, the volume change dV and the corresponding pressure change dp. By analogy, the given density $\rho$ can be split into mass m and volume V.

Furthermore, it has been detected within the scope of the disclosure that the equations (Eqn. 1) and (Eqn. 2) mentioned above can only be applied to the human or animal skull if the structure of the corresponding biological material is taken into account. As a result, it has been detected that performing an acoustic spectroscopy on the biological material is not sufficient by itself to determine the intracranial compliance of the biological material in an adequate manner. Instead, it is necessary to also consider the expansion of the human or animal skull caused by the intracranial pressure during the systolic phase. It is heavily dependent on different factors, such as age, intracranial pressure and/or the presence of at least one pathological condition, and, as has been proven by volunteers during bed rest, is in the range of up to 20 μm. It has been detected within the scope of the disclosure that the expansion and contraction of the skull are caused by intracranial pressure changes and that they are offset by the stiffness of the surrounding skull. Measuring the expansion of the human or animal skull during the systolic phase can provide valuable information regarding a changed intracranial pressure, the cerebral blood flow and/or at least one pathological condition.

The term "Method and device for a non-invasive determination and/or monitoring" relates to a method for detecting the intracranial compliance of a biological material, by means of which an adequately precise, reliable determination of the intracranial compliance is possible in an adequate measuring range. It is conceivable that the method is based on the detection of the intracranial compliance and its change, which can be an improvement or a deterioration. Preferably, this change is detected over time. More preferably, the detection is repeated once or at a regular or irregular interval and is carried out temporarily or permanently, in order to be able to detect the change in intracranial compliance. This is of particular importance because the biological material to be examined is not a static system. Additionally, it can be monitored under which conditions and/or influences the intracranial compliance change progresses or decelerates. Furthermore, the origin and/or cause of this change can be shown. The method according to the disclosure can also comprise additional steps to be carried out after or between the explicitly named essential steps a) to d). The method is preferably automatable.

The term "biological material" relates to a human or animal skull known to the person skilled in the art. Furthermore, general and specific features of the anatomical and/or physiological environment of the skull and/or of the brain and the vascular system of the brain are known to the person skilled in the art.

The term "determination of the intracranial compliance" relates to the detection of a current value of the intracranial compliance. The determination is preferably carried out in a semi quantitative, quantitative, direct and/or indirect manner. By means of the detection of the intracranial compliance, it is thus possible to indirectly receive further information on the material to be examined, for example.

The term "monitoring of the intracranial compliance" relates to the tracking and/or the prediction of the determined value of the intracranial compliance. The monitoring is displayable numerically and/or graphically, for example, but not exclusively. To increase the precision of the monitoring, it is preferably carried out at a regular or irregular interval or permanently. The advantage of a monitoring carried out over a longer period of time is that a prediction, a prognosis and/or an assessment of a change in intracranial compliance can be made.

It is known to a person skilled in the art that a determination and/or a monitoring can usually not be 100 percent correct. The term thus relates to a statistically significant probability regarding the precision of the detecting or the tracking and/or prediction. Whether such a determination and/or monitoring is statistically significant can be determined by a person skilled in the art without an inventive step by means of methods known in professional circles. Statistical evaluation tools are an example, such as the assessment of the confidence interval, the p value, the student's t-test, the Mann-Whitney U test, etc. The corresponding intervals are at least 90%, at least 95%, at least 97%, at least 98% or at least 99% correct. The p values are preferably 0.1, 0.05, 0.01, 0.005 or 0.0001. The determination and/or the monitoring of the intracranial compliance within the scope of the present disclosure is preferably at least 80%, 90%, 95%, 96%, 97%, 98%, 99%, 99.5%, 99.6%, 99.7%, 99.8%, 99.9%, 99.95%, 99.99% or 100% correct.

The term "intracranial compliance" is used as an interchangeable synonym for the term "intracranial volume-pressure relationship", both of which are known to a person skilled in the art and which describe the connection between intracranial volume and intracranial pressure in a human or animal skull. Intracranial pressure increases are usually buffered by displacing venous blood and cerebrospinal fluid from the skull when the intracranial volume (ICV) increases. It is known to the person skilled in the art that the intracranial compliance depends on various factors, such as the pressure change in the skull, the elastance (the inverse of compliance), the hydraulic compliance (the relationship between a momentary change in intracranial volume and/or a corresponding change in intracranial pressure) and/or the movement of the skull bones at their sutures. Furthermore, it is known that the intracranial pressure increases non-linearly with the increase of the intracranial volume, as is described by the pressure-volume index. Furthermore, standard values are known to the person skilled in the art.

The method according to the disclosure comprises a step a) for performing an acoustic spectroscopy of the biological material, wherein several acoustic transmitting signals of different frequencies and/or amplitudes are sent into the biological material and corresponding reflected and/or transmitted acoustic receiving signals of different frequencies and/or amplitudes are received after having passed through the biological material. In a further step, the acoustic transmitting signals are compared with the corresponding acoustic receiving signals, wherein a function in n-dimensions, which is characteristic for the biological material, and the time-of-flight values and/or the phase shift are determined as an equivalent. It is conceivable that, in addition to the time-of-flight values, the frequency shift of the assigned acoustic signal is determined from each transmitting and receiving signal pair. In other words, this means that from each transmitting and receiving signal pair of a corresponding or specific frequency, the method according to the disclosure ultimately determines a data pair from the respective time-of-flight and, if applicable, frequency shift.

From each transmitting and receiving signal pair of a corresponding or specific frequency, the method according to the disclosure ultimately determines a data pair from the respective time-of-flight values and, if applicable, the frequency shift, and, if necessary, stores it in a correspondingly configured device with the corresponding frequency. Carrying out the method accumulates very large result data records, because for each frequency and the assigned transmitting and receiving signal pair, one result data record with the respective time-of-flight and, if applicable, frequency shift is determined, stored and/or graphically displayed. Thus, it is preferably intended that a data reduction is carried out; for example, a reduced data record is derived from the detected result data record in a data reduction device, wherein the reduced result data record characteristically displays the detected result data record and has a smaller data volume. How the data reduction is carried out is generally arbitrary and subject to the expertise of the person skilled in the art.

The term "acoustic spectroscopy" relates to the acoustic examination of a medium by drawing conclusions from the changes of acoustic waves and/or vibrations in the sound frequency range (20 kHz to 1 GHz), in particular in the range of ultrasonic waves and/or longitudinal waves, wherein the changes are based on the interactions of the structures contained in the biological material with the acoustic waves and/or the vibrations. In this manner, it is possible to noninvasively examine the biological material by means of the acoustic spectroscopy, in order to determine changes in the structure of the medium in this manner. The acoustic spectroscopy is preferably carried out with the aid of a suitable means, which is partly or fully disposed on the biological material, and which is suitable for emitting, transmitting, enhancing and/or receiving vibrations in the material, such as an acoustic transmitting element and/or receiving element.

It is also intended according to the disclosure that—based on the comparison of the corresponding transmitting and receiving signal pairs, preferably based on the received corresponding result data records—it possible to determine a function in n-dimensions, which is characteristic for the biological material, and the time-of-flight values and/or the phase shift as an equivalent. It is known to a person skilled in the art that the terms "n-dimensional function" and "function in n-dimensions" can be used as interchangeable synonyms. Furthermore, suitable methods and means for detecting the time-of-flight values, such as, for example, but not limited to, the travel time measurement, are known to a person skilled in the art. The terms "travel time measurement" and "time-of-flight" are used as interchangeable synonyms for a method for an indirect distance and/or speed measurement by measuring the time a signal needs to pass through the measuring section. Preferably, essentially only time differences are determined, such that the travel time measurement constitutes a relative time system without a defined zero point.

Within the scope of the disclosure, it has been detected that the speed of the wave propagation directly depends on the characteristics of the biological material and thus indirectly reflects its characteristics. Thus, it is conceivable that the density of the biological material changes because venous blood is displaced from the human or animal skull. Furthermore, it is conceivable that the speed of the wave propagation changes because of the cerebral blood flow (diastolic/systolic) and/or a cerebral tissue perfusion.

Subsequently, an expansion of the biological material is determined in step c), wherein the linear expansion and/or volume expansion of the biological material is measured. This step is of particular importance because it has been detected within the scope of the disclosure that because of the skull expansion, a phase change and/or time dilatation or time contraction must occur during the performance of an acoustic spectroscopy as an equivalent of the sent signal. The expansion of the skull to be examined is in the range of up to 20 μm and depends on different factors, such as age, intracranial pressure and/or pre-existing medical conditions. Preferably, the expansion is determined during the systolic phase. The determination of the expansion is preferably carried out in a semi quantitative, quantitative, direct and/or indirect manner. Furthermore, it is conceivable that a means, which is suitable for the determination of the expansion of the biological material, is used, by means of which the linear expansion and/or volume expansion of the biological material can be adequately measured in a precise manner. It is conceivable that this suitable means directly or indirectly measures the expansion using the means and/or methods known from the state of the art.

The functional relation is displayable in a two-dimensional function as a trend for example, but not exclusively, having a value progress over time, for instance in a linear, logarithmic, exponential, logistical, polygenic function and/or a combination of the above.

The term "comparison" relates to the comparing of corresponding values with each other, in particular the acoustic transmitting signal with the corresponding acoustic receiving signal. It shall be understood that comparisons drawn in this case relate to a comparison of corresponding parameters and/or values.

Within the scope of the disclosure, the comparison, the determination and/or the detection are preferably carried out in a computer-aided manner. For carrying out these steps, for example the steps b), c) and/or d), in a computer-aided manner, the person skilled in the art may use all their known tools, such as a computer and/or a computer program. Additionally, a computer program can evaluate the corresponding result, for example, it can automatically deliver an assessment of the value. Furthermore, it is conceivable that the steps b) and/or d) are aided by an analysis unit, an assessment unit and/or an evaluation unit, for example. Preferably, it is also possible to consider successive acoustic transmitting signals and/or acoustic receiving signals in the comparison, such that based on this comparison, a prediction regarding how the condition changes in relation to time can be made.

Within the scope of the disclosure, it is understood that the result of the method, meaning the determination of the intracranial compliance, directly or indirectly depends on the biological material to be examined. Thus, it is conceivable that a slight and insignificant change, a large and significant change and/or no change in intracranial compliance of the biological material is an indicator for a change in intracranial compliance in relation to time. A change in intracranial compliance can preferably be an improvement and/or a deterioration of said compliance. In this context, it is conceivable that the result of the method is displayable as a time specification via an absolute and/or a relative value.

In the last step, the determination of the intracranial compliance of the biological material based on the comparisons drawn in step b) and the measurement carried out in step c) takes place. The person skilled in the art understands that the determination can be effected by calculating, counting back, deriving and/or concluding, in particular based on one or several assumptions. Furthermore, it is conceivable that the determined result is assessed.

By means of the method according to the disclosure, it is thus possible to determine and/or monitor the intracranial compliance of a human or animal skull in a simple, quick, reliable and adequately precise manner in order to detect the intracranial compliance temporarily or permanently, for example. It is also possible to perform this determination and/or monitoring live. The simplicity of the method according to the disclosure allows not only specially trained medical personnel to use the disclosure, but everyone—be it in private households for self-control or on the part of emergency medical technicians, nurses and/or assistant workers. Advantageously, it has been detected within the scope of the disclosure that the method has a measuring range of several microseconds having a resolution of individual picoseconds and it thus constitutes an adequate tool for non-invasive determination and/or monitoring of the intracranial compliance of a human or animal skull, which also significantly contributes to supporting the medical diagnosis in the case of intracranial pressure, cerebral blood flow and/or at least one pathological condition. In this manner, it is possible to recognize a change in intracranial pressure in time and treat it adequately, which particularly positively influences the mobility, mortality and/or prognosis of the patient.

Advantageous embodiments of the disclosure, which can be realized on their own or in combination, are indicated in the dependent claims.

In an embodiment of the disclosure, it is conceivable that the method additionally comprises:
 e) Detecting the intracranial pressure, the cerebral blood flow and/or a pathological condition of the biological material based on the intracranial compliance detected in step d).

By means of this embodiment, it is possible to obtain additional important factors from the detected intracranial compliance via calculating, counting back, deriving and/or concluding (with assumptions).

The term "intracranial pressure (ICP)" relates to the pressure inside the skull and thus in the brain tissue and cerebrospinal fluid. It is known to a person skilled in the art that the intracranial pressure is crucial for the brain tissue perfusion and thus for the brain function in general, because it counteracts the pressure with which the blood is pumped into the brain. Additionally, the person skilled in the art knows about the reciprocal relationship between the volumes of cerebrospinal fluid and blood as Monro-Kellie doctrine, according to which the volume of brain, blood and cerebrospinal fluid is constant with an intact skull. Consequently, an increase in one component causes a decrease in one or both other components. Furthermore, standard values are known to the person skilled in the art. Preferably, the intracranial pressure is derivable from the equations (Eqn. 1) and (Eqn. 2) mentioned above and depends on the linear expansion and/or volume expansion of the skull.

The terms "cerebrospinal fluid (CSF)", "liquor cerebrospinalis" and "liquor" are known to a person skilled in the art and are used as interchangeable synonyms within the scope of the disclosure for the body fluid that surrounds the brain and spinal cord, colloquially called brain fluid, cerebral fluid or spinal fluid. Furthermore, standard values are known to the person skilled in the art.

The term "cerebral blood flow (CBF)" is known to a person skilled in the art and relates to a measure for the blood supply to the brain in a given period of time. Furthermore, standard values are known to the person skilled in the art. It is known from the state of the art that the cerebral blood flow is approx. 15 percent of the cardiac output and amounts to approx. 750 ml per minute. Additionally, the total cerebral blood flow is distinguishable from the actual cerebral blood flow within the scope of the disclosure. Preferably, the cerebral blood flow is calculated from the equations (Eqn. 1) and (Eqn. 2) mentioned above.

The term "pathological condition" relates to any damages to the human or animal skull and is thus of particular importance. A pathological condition is, for example, a traumatic brain injury, brain damage, stroke, hyperemia, cerebral edema, insufficient blood flow, cerebral ischemia, brain hemorrhage, in particular intracranial, intracerebral, parenchymal and/or extracerebral brain hemorrhage, subarachnoid hemorrhage, thrombosis, irritation and/or changes of blood vessels, decreased perfusion and/or a tissue perfusion of the brain tissue. Preferably, the pathological condition is derivable from the equations (Eqn. 1) and (Eqn. 2) mentioned above. More preferably, it is possible to locate the position of the pathological condition in the human or animal skull.

By means of this additional step, it is thus possible to obtain additional crucial values for the timely detection and adequate treatment of a patient from the previously determined intracranial compliance.

In a further embodiment of the disclosure, it is conceivable that the method additionally comprises:

f) Displaying the detection carried out in step d) and/or in step e).

By means of this embodiment, it is possible to numerically and/or graphically display the detected values to simplify the understanding of the detection carried out in step d) and/or in step e). A person skilled in the art is aware of suitable means for displaying an output of a value. Step f) can additionally be supported by an output unit.

In a further embodiment of the disclosure, it is conceivable that the acoustic transmitting signals are emitted at a first position of the biological material and that the acoustic receiving signals are received at a second position of the biological material and that the first and second position are identical or disposed opposite each other. By means of this embodiment it is possible to dispose the means necessary for carrying out the method so as to be space-saving and comfortable for the patient to be examined, whereby the aforementioned values are simultaneously detected in a reliable manner.

Furthermore, it is conceivable that the acoustic spectroscopy and/or the determination of the expansion of the biological material are essentially carried out in the area of the left and right cerebrum and the longitudinal cerebral fissure. It has been detected within the scope of the disclosure that the equations (Eqn. 1) and (Eqn. 2) mentioned above allow the best possible detection of the previously mentioned values, if the structure of the human or animal skull is considered. It has been detected that the impact of skin, muscle, skull bone and/or cerebrospinal fluid on acoustic signals can be neglected and that they can therefore be regarded as constants. The areas of the left and right cerebrum and the longitudinal cerebral fissure, including the part of the cerebrospinal fluid, however, heavily depend on the cardiac cycle and the perfusion of the brain tissue. Thus, these areas of the biological material are suitable for performing the method according to the disclosure.

The term "essentially" means that the value or area in question is subject to only a slight, in particular insignificant, change, shift and/or deviation. It is conceivable, for example, that the acoustic spectroscopy and/or the determination of the expansion of the biological material is carried out at a position slightly deviating from the preferred area of the left and right cerebrum and the longitudinal cerebral fissure, meaning that it has no effect or an insignificant effect on the detection to be carried out.

Furthermore, it is conceivable that the acoustic spectroscopy and/or the determination of the expansion of the biological material are essentially performed in the direction of the frontal plane (coronal) of the skull, slightly above the external ear canal. Thus, it has been detected within the scope of the disclosure that the areas most suitable for performing this measurement method are the surfaces which are located in the direction of the frontal plane of the skull, slightly above the external ear canal. By means of this embodiment the intensity and/or strength of the acoustic wave can be maximized, as this area of the cranial system is characterized by the lowest degree of suppression of acoustic waves. Consequently, it is very probable that a full echo is received from the opposite skull bone, such that based on the aforementioned analyses, a simplified, layered structure of the cranial system can be adopted.

It is assumed that the definitions and/or the explanations of the terms stated above apply to all following aspects described in this description, unless indicated otherwise.

Furthermore, the disclosure proposes a device for a non-invasive determination and/or monitoring of the intracranial compliance of a biological material according to any one of the preceding method claims. The device according to the disclosure comprises a first means for performing an acoustic spectroscopy of the biological material, wherein the first means comprises an acoustic transmitting element for transmitting several acoustic transmitting signals of different frequencies and/or amplitudes into the biological material and an acoustic receiving element for receiving corresponding reflected and/or transmitted acoustic receiving signals of different frequencies and/or amplitudes after having passed through the biological material, and wherein the biological material is a human or animal skull. Furthermore, the device comprises an evaluation unit for comparing the acoustic transmitting signals with the corresponding acoustic receiving signals, wherein a function in n-dimensions, which is characteristic for the biological material, and the time-of-flight values and/or the phase shift are determinable as an equivalent. Furthermore, the device comprises a second means for determining the expansion of the biological material, wherein the second means comprises a measuring device, such as, but not limited to a strain gauge, a pressure sensor, a capacitive sensor or the like for measuring the linear expansion and/or the volume expansion of the biological material. Lastly, the device further comprises an analysis unit for determining the intracranial compliance of the biological material based on the comparisons drawn and the measurements carried out.

The device according to the disclosure is preferably self-learning and/or self-calibrating in order to obtain the best possible determination and/or monitoring of the intracranial compliance. Equally preferably, the device can be used for Acoustocerebrography (ACG). More preferably, the device is suitable for temporarily or permanently determining and/or monitoring the biological material.

The term "first means" relates to an arbitrary means known from the state of the art to a person skilled in the art, which is suitable for emitting, transmitting, enhancing and/or receiving vibrations in the biological material in the sound frequency range, in particular the range of ultrasonic waves and the range of longitudinal waves. The means is preferably partly or fully disposed on the biological material.

Preferably, the first means is an acoustic transmitting element for transmitting several acoustic transmitting signals of different frequencies and/or amplitudes into the biological material and/or an acoustic receiving element for receiving corresponding reflected and/or transmitted acoustic receiving signals of different frequencies and/or amplitudes after having passed through the biological material.

The term "second means" relates to an arbitrary means known from the state of the art to a person skilled in the art, which is suitable for measuring the expansion of the biological material, in particular the linear expansion or/and volume expansion of the biological material. The measurement can be carried out using means and/or methods known from the state of the art in a direct or indirect manner."

The term "evaluation unit" relates to a unit which is suitable for comparing the acoustic transmitting signals with the corresponding acoustic receiving signals. Suitable evaluation units are known to a person skilled in the art, for example a computer and/or a computer program. In addition, a computer can assess the result of the comparison.

The term "analysis unit" relates to a unit which is used for assessing or detecting the intracranial compliance of the biological material. The analysis unit is a computer or a computer program, for example.

The device according to the disclosure is advantageous in the sense that it has an adequately accurate sensitivity for a simple, quick, reliable and adequately accurate determination and/or monitoring of the intracranial compliance of the biological material, which can be carried out temporarily or permanently. It is also possible to perform this determination and/or monitoring live. Additionally, the device advantageously has a measuring range of several microseconds having a resolution of individual picoseconds and thus constitutes an adequate instrument for non-invasive determination and/or monitoring of the intracranial compliance of the biological material, which significantly contributes to supporting the medical diagnosis in the case of intracranial pressure, cerebral blood flow and/or pathological conditions. Subject to everyday use, the device is also sturdy enough to last over the long term.

Advantageous embodiments of the disclosure, which can be realized on their own or in combination, are indicated in the dependent claims.

In an embodiment of the disclosure, it is conceivable that the analysis unit is configured to detect the intracranial pressure, the cerebral blood flow and/or a pathological condition of the biological material (as described in more detail above) based on the detected intracranial compliance.

Furthermore, it is conceivable that an output unit for illustrating the detection carried out by the analysis unit is comprised. The term "output unit" relates to a unit which is suitable for illustrating the detected values. By means of this embodiment, it is possible to numerically and/or graphically illustrate the intracranial compliance and the values relating therefrom, meaning intracranial pressure, cerebral blood flow and/or a pathological condition, in order to simplify the understanding of the detection. Suitable output units for illustration are known to a person skilled in the art.

Furthermore, it is conceivable that the acoustic transmitting element is disposed at a first position of the biological material and that the acoustic receiving element is disposed at a second position of the biological material and that the first and second position are identical or disposed opposite each other, as previously described in more detail.

Furthermore, it is conceivable that the acoustic spectroscopy and/or the determination of the expansion of the biological material are essentially carried out in the area of the left and right cerebrum and the longitudinal cerebral fissure, as previously described in more detail.

In a further embodiment, it is conceivable that the first means, the second means, the evaluation unit, the analysis unit and/or the output unit are disposable in one component. Preferably, the component is an acoustic hybrid sensor, hair band, headband and/or headphones. This embodiment has the advantage that the device is compact, easy to handle and easy to transport.

In another embodiment, it is conceivable that the device is realized so as to be rotatable and/or moveable in order to change the position and to achieve an improved detection of the intracranial compliance and the values resulting therefrom, meaning intracranial pressure, cerebral blood flow and pathological conditions, and especially to locate the pathological conditions.

Further details, features and advantages of the disclosure are apparent from the following description of preferred embodiments in connection with the dependent claims. The respective features can be realized on their own or in combination with each other. The disclosure is not limited to the exemplary embodiments. The exemplary embodiments are shown schematically in the figures. Identical reference signs in the individual figures refer to identical or functionally identical elements or elements corresponding to each other in their function.

In the figures:

FIG. 1 shows a schematic view of the device according to the disclosure; and

Figure 2A:
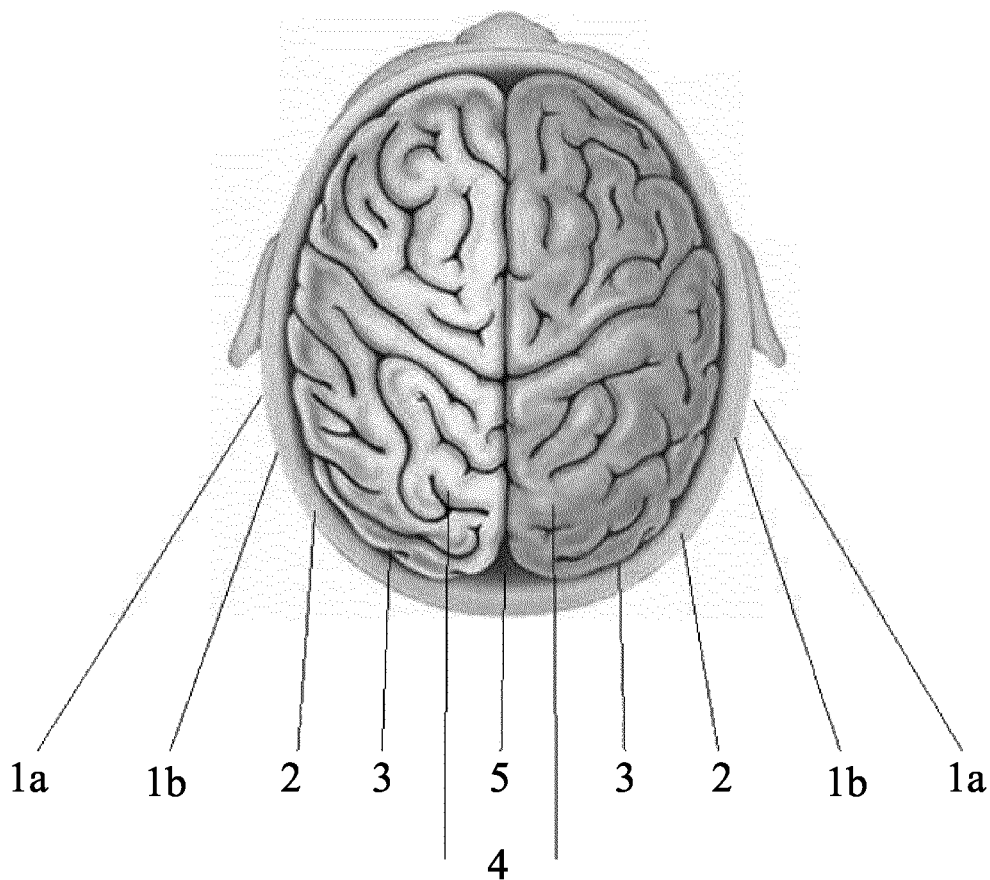
Figure 2B:
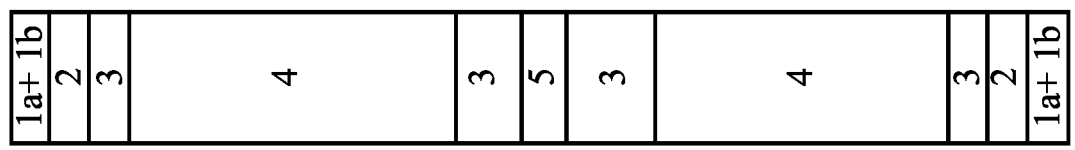
Figure 3A:
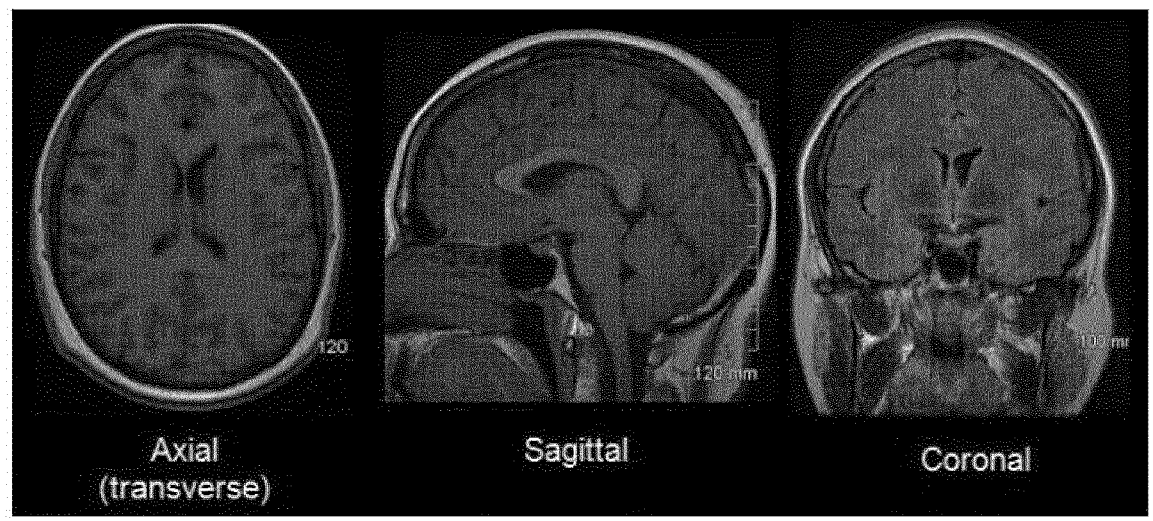
Figure 3B:
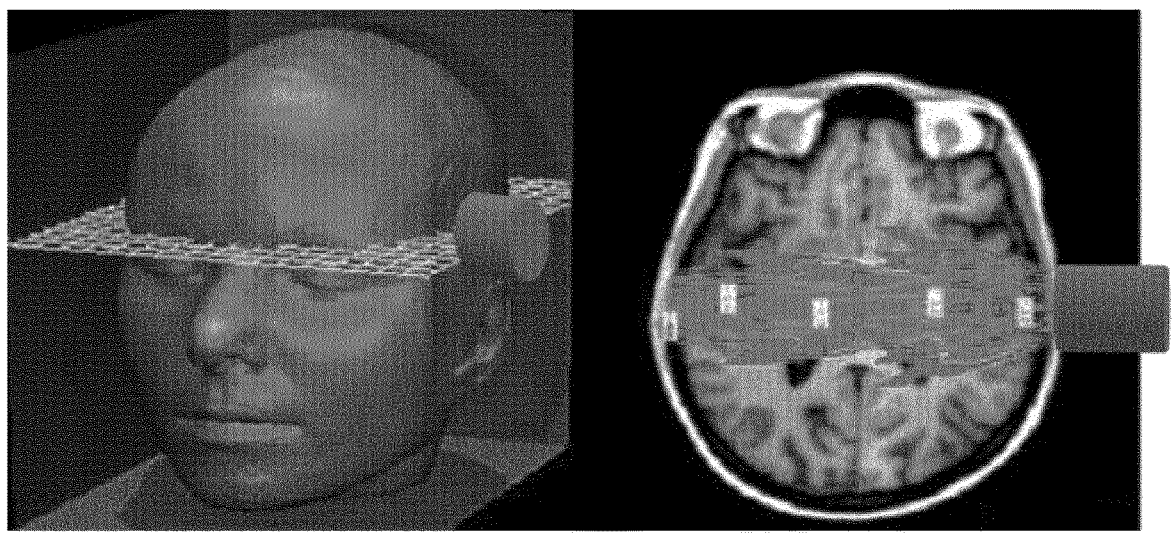
Figure 4:
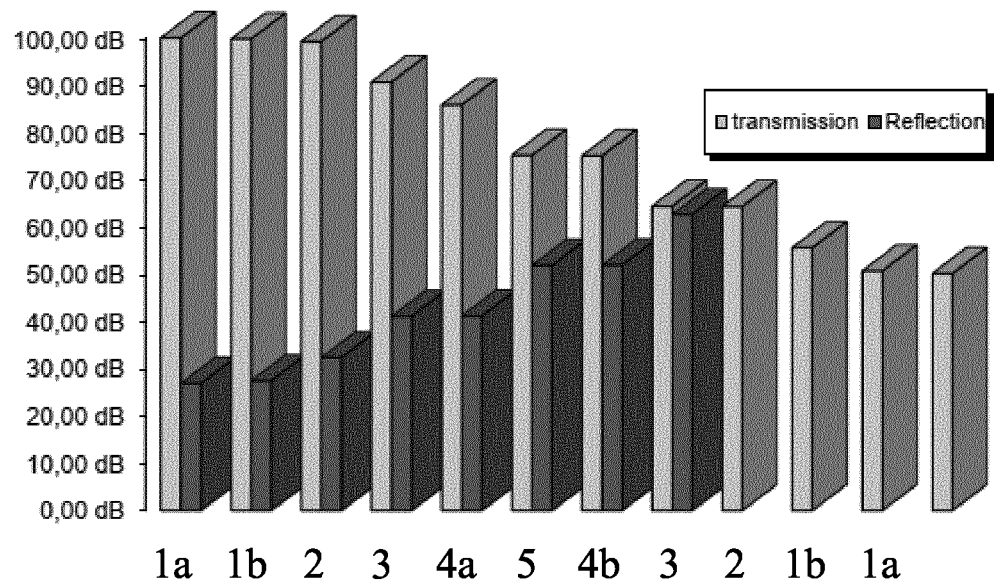
Figure 6:
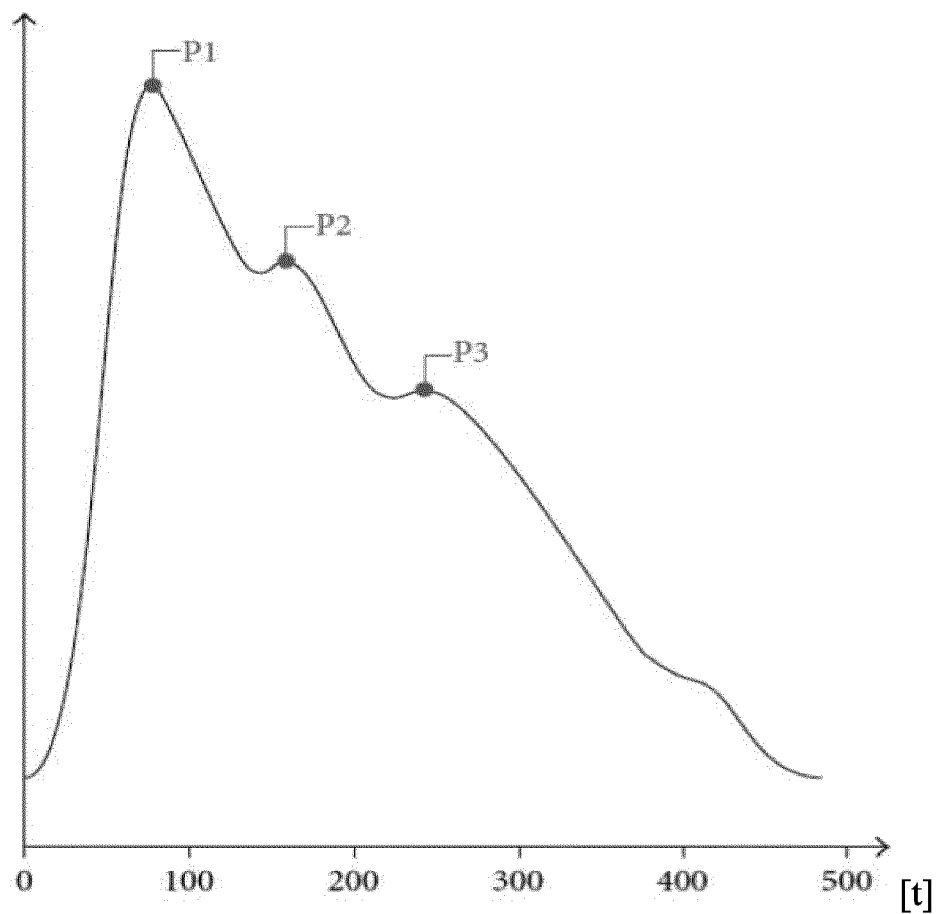
Figure 5:
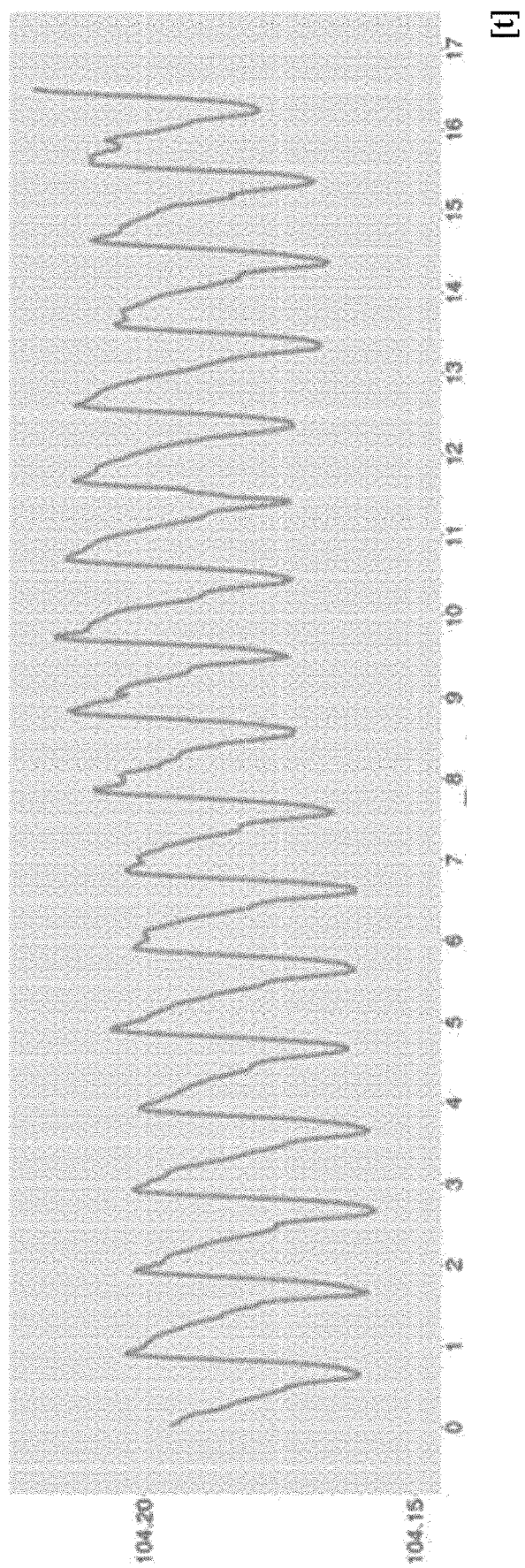

FIG. 2 shows a schematic view of the structure of the human skull (FIG. 2A) and a correspondingly layered model of the human skull from FIG. 2A (FIG. 2B); and FIG. 3 shows a first (FIG. 3A) and a second (FIG. 3B) schematic view of the most suitable area of the human skull for carrying out the method according to the disclosure or for disposing the device according to the disclosure; and FIG. 4 shows an overview of the signal attenuation along the measurement path in the human skull; and FIG. 5 shows a graphic view of the data collected from a 72-year-old patient; and FIG. 6 shows a graphic view of the propagation of the cardiac pulse pressure signal, in particular an intracranial pressure measurement recorded by an intracranial pressure probe.

FIG. 1 schematically illustrates a device 01 according to the disclosure disposed on a biological material 02, a human skull. It can clearly be seen in FIG. 1 that device 01 has a first means 10 which comprises an acoustic transmitting element 11, which is disposed on a first position X1, and an acoustic receiving element 12, which is disposed on a second position X2. It can clearly be seen that the first and second position X1, X2 are disposed opposite each other and that the acoustic spectroscopy is performed in the direction of the frontal plane (coronal) of skull 02, slightly above the external ear canal.

Furthermore, device 01 has a second means 30 having a measuring device 31, such as a strain gauge, a pressure sensor, a capacitive sensor or the like. An evaluation unit 20 and an analysis unit 40 are also integrated in FIG. 1. It is also conceivable that they are intended as non-integral parts. The values recorded by device 01 can additionally be transmitted to an output unit (now shown).

The following embodiments only serve to illustrate the disclosure. They are not intended to limit the subject matter of the claims in any way.

EXAMPLE 1: THE BASICS OF THE CONCEPT ACCORDING TO THE DISCLOSURE, ACOUSTOCEREBROGRAPHY (ACG)

As described in detail above, it has been detected within the scope of the present disclosure that the concept according to the disclosure, namely Acoustocerebrography (ACG), can be applied to the biological material. It was thus detected that using several frequencies shows the dispersive character of the brain tissue and provides some interpretation of the signal changes. Dispersion is an effect in which the non-linear, frequency-dependent compressive modulus of the medium results in different propagation speeds for different sound frequencies. In non-linear material, such as biological tissue and, in particular, human brain tissue and animal brain tissue, an effect of longitudinal wave dispersion can be clearly observed and measured. It is such an effect, in which the compressive modulus of the non-linear, frequency-dependent medium results in different propagation speeds for different sound frequencies. As described in detail above, the properties of the compressive modulus depend on the specific characteristics of the medium, such as composition, mixture concentration, distribution and/or, in some cases, chemical composition, such that the pattern of frequency-dependent propagation speeds can be used to identify the medium.

In order to apply the equations (Eqn. 1) and (Eqn. 2) mentioned above to the human or animal skull, the structure of the corresponding biological material must be taken into consideration. In FIG. 2A, the structure of the human skull is roughly illustrated, and in FIG. 2B, a correspondingly layered model of the human skull from FIG. 2A is roughly illustrated.

The tissue structures of the human skull $1a$, $1b$, $2$, $3$ (with ventricles), $4$ and $5$ illustrated in FIGS. 2A and 2B are explained in Table 1 below:

TABLE 1

Overview of the impact of the tissue structures from FIGS. 2A and 2B on the change of the time-of-flight of the acoustic wave

| No. | Tissue structure | Size [mm] | Impact of the tissue structure on acoustic examination |
|---|---|---|---|
| 1a + 1b | Skin + Muscle | approx. 2.5 | No |
| 2 | Skull bone | approx. 2.5 | No |
| 3 | cerebrospinal fluid (CSF) | approx. 25.0 (with ventricles) | Partially - Yes |
| 4 | left and right cerebrum | approx. 67.0-69.0 | Yes |
| 5 | Cerebral fissure | approx. 1.5 | No |

Table 1 clearly states that the structures skin ($1a$), muscle ($1b$), skull bone ($2$) and cerebrospinal fluid of the human skull, which are illustrated in FIGS. 3A and 3B, have no impact on the performed acoustic spectroscopy and can therefore be regarded as constants. However, the left and right cerebrum ($4$), the longitudinal cerebral fissure ($5$), including the proportion of cerebrospinal fluid ($3$), have an impact on the performed acoustic spectroscopy, the impact strongly depending on the cardiac cycle and the blood circulation in the brain tissue. These zones are the "point of interest" for further examinations.

The data should be obtained with the time-of-flight method according to the following equation (Eqn. 3). If we have a set of tissue layers T, then the total propagation time is obtained by summing the propagation time for each tissue in the set.

$$t(f) = \Sigma_{i \in T} t_i(f) \qquad \text{(Eqn. 3)}$$

The concept according to the disclosure and the model based on said concept can easily be upgraded or modified, for example by adding additional tissue layers. If precise and detailed dispersion data is available, the dispersion for a specific tissue can be modeled as a non-linear function of frequency. For a given tissue i, the propagation time for frequency f, $t_i(f)$ can be calculated according to the following equation (Eqn. 4).

$$t_i(f) = \frac{d_i}{c_i(f)} = \frac{d_i}{c_{0i} + (f - f_{0i})\Delta_i} \qquad \text{(Eqn. 4)}$$

In the equation (Eqn. 4) stated above, d is the depth of the tissue travelled through by the acoustic wave, $c_{0i}$ is the basic speed defined at a base frequency $f_{0i}$, and $\Delta_i$ is the dispersion trend of the tissue, which characterizes the dependence of the frequency on the propagation speed. The signal is transmitted by an ultrasound probe and is recorded either by another acoustic wave (transmission) or by the same acoustic wave (reflection). As described above, the speed of a transmitted signal depends on the medium. Based on the anatomical analyses of the human skull-brain-system, it can be demonstrated that depending on the region, there are very different conditions for the propagation of acoustic waves. This led to considerations regarding the optimization of the direction of the tissue examination. It was thus detected that the direction of the frontal plane (coronal), which is illustrated in FIG. 3A, should be chosen for transmission or reflection measurements.

Limitations related to the minimization of the intensity of ultrasonic waves have induced the search for such areas in the cranial system which are characterized by the smallest acoustic wave suppression. The analysis shows that the areas most suitable for the implementation of this measurement method are the surfaces located slightly above the external ear canal, as can be seen in FIG. $3b$. Choosing such a measuring direction very probably causes a full echo from the opposite skull bone. Based on the above-stated analyses in FIG. 2A and FIG. 2B and Table 1, a simplified, layered structure of the cranial system can be adopted.

By adopting the layer model of the human cranium (illustrated above in FIG. 2A and FIG. 2B and in Table 1) as an input—together with the physical values of the different cranial tissues shown below in Table 2—the propagation times of the acoustic signal, as well as the signal attenuation along the measurement path through these structures, can be determined.

TABLE 2

The basic parameter assumptions for the human skull-brain-model

| | Density ρ [kg/m³] | c [m/s] | Z [kg/(m² * s)] | e.g. coefficient [dB/(cm * MHz)] | |
|---|---|---|---|---|---|
| | | | | 1 MHz | 10 MHz |
| Cerebrum tissue | 1030 | 1515 | 1560450.000 | 1 | 8 |
| Skull bones | 1900 | 4080 | 7752000.000 | 10 | 60 |
| CSF | 1007.5 | 1498 | 1509235.000 | 0.003 | 0.22 |
| Water | 997 | 1483 | 1478551.000 | 0.003 | 0.22 |
| Blood | 1057 | 1580 | 1670060.000 | 0.2 | 3.8 |
| Skin + Fat | 930 | 1480 | 1376400.000 | 1.5 | — |
| Muscle | 1002 | 1580 | 1583160.000 | 0.7 | — |

In FIG. 4, the signal attenuation along the measurement path in the human skull is illustrated for the structures illustrated above in FIGS. 2A and 2B, namely skin ($1a$), muscle ($1b$), skull bone ($2$), cerebrospinal fluid ($3$), left cerebrum ($4a$), right cerebrum ($4b$) and the longitudinal cerebral fissure ($5$). Furthermore, a human head model of the ultrasonic signal attenuation and the expected time-of-flight along the measurement path is illustrated in Table 3 below.

TABLE 3

Human head model of the ultrasonic signal attenuation and expected time-of-flight along the measurement path

| Time | |
|---|---|
| 0.533 | Skin |
| 1.251 | Muscle |
| 0.613 | Skull bones |
| 6.476 | CSF |
| 42.384 | left cerebrum |
| 1.669 | Fissure |
| 42.384 | right cerebrum |
| 6.476 | CSF |
| 0.613 | skull bones |
| 1.251 | muscle |
| 0.533 | skin |
| 104.183 µs | total |

Taking into account a transmission method, the measuring process includes the "introduction" of an acoustic wave into the central cerebral system at the selected position X1 (shown in FIGS. 3A and 3B) and, subsequently, the reception at the opposite position X2, depending on the direction of the spread of the acoustic beam. Thus, this method preferably requires two ultrasound probes—one for emitting and one for receiving the acoustic signal.

The cerebrovascular system is very complex and thus, the state of the blood supply of the brain largely influences its physical and chemical parameters. The intracranial pressure depends on intracranial fluid volumes, tissue volumes and the pulsating volumes, which are induced by the arterial blood pulsation within the skull. By known normal brain blood circulation or cerebral blood flow (CBF), e.g. of 50 mL/100 g/min, it has been detected that for an average brain weight of 1,375 g, the mean CBF value is at approx. 690 ml per minute. This results in a blood value of approx. 11.6 ml per second (estimated as the volume per heartbeat). Based on this, the time-of-flight measurement and the speed of sound changes and/or acoustic wave changes can be calculated on the basis of a standard cranial tissue perfusion CBF. The bone movement detected with volunteers is up to 20 µm during bed rest and can be calculated by means of the following equation (Eqn. 5).

$$c_{path}^2 = \frac{(K_{norm}(1-x) + K_{path} * x)}{(\rho_{norm}(1-x) + \rho_{path} * x)} \quad \text{(Eqn. 5)}$$

Let's take a very simplified model, as shown in the equation (Eqn. 6) below. A standard CBF with 50 mL/100 g/min means that with every heart rate, e.g. 60 beats per minute (bpm), between diastole and systole, approx. 8% to 10% of the mass will be exchanged.

$$\frac{CBF}{bpm} * \rho_{Blood} \Rightarrow \frac{50 \text{ ml}}{60 \text{ bpm}} * \frac{1.057 \text{ g}}{cm^3} = 0,88 \text{ g} \quad \text{(Eqn. 6)}$$

Furthermore, it can be attempted to estimate the change of speed of the acoustic waves according to the equation (Eqn. 5) above. Assuming that approx. 10% of CSF is periodically exchanged with the blood according to the normal perfusion values, it can be attempted to calculate the time-of-flight changes of the acoustic wave. The corresponding K values of CSF and blood can be calculated from the known c and ρ according to the following equations (Eqn. 7) to (Eqn. 10).

$$K_{CSF} = c_{CSF}^2 * \rho_{CSF} = 1498^2 * 1007.5 = 2.2608* \quad \text{(Eqn. 7)}$$

$$K_{Blood} = c_{Blood}^2 * \rho_{Blood} = 1580^2 * 1057 = 2.6386* \quad \text{(Eqn. 8)}$$

$$c_{sys}^2 = \frac{(K_{CSF}(1-x) + K_{Blood} * x)}{(\rho_{CSF}(1-x) + \rho_{Blood} * x)} \quad \text{(Eqn. 9)}$$

$$c_{sys} = \sqrt{\frac{(2.2608*(1-0,1) + 2.6386*0,1)*10^9}{(1007.5*(1-0,1) + 1057*0,1)}} = \quad \text{(Eqn. 10)}$$

$$1506.7563 \left[\frac{m}{s}\right]$$

Assuming the CSF area (meaning the area, where the brain tissue expands due to the pulsation) to be 1 cm overall, the diastolic travel time can be calculated with the following equation (Eqn. 11):

$$t_{dia} = \frac{l}{c_{CSF}} = \frac{0.01}{1498} = 6.67556 \text{ } \mu s \quad \text{(Eqn. 11)}$$

Together with the result from equation (Eqn. 10) and based on the assumption of a maximum expansion of the skull by 20 µm, the following equation (Eqn. 12) allows for the calculation of an expected systolic time-of-flight (within the faster medium, as 10% of CSF is exchanged with blood).

$$t_{sys} = \frac{l}{c_{sys}} = \frac{0.0102}{1506.75} = 6.76953 \text{ } \mu s \quad \text{(Eqn. 12)}$$

The equations (Eqn. 11) and (Eqn. 12) listed above result in an acoustic time-of-flight of $c_{CFS}$=1498 m/s during the diastolic phase. During the systolic phase (with x=10%=0.1), an acoustic time-of-flight of $c_{sys}$=1506.76 ms is calculated. Despite the fact that the acoustic wave is 1506.76−1498=8.76 m/s faster during the systolic phase, an increasing time-of-flight waveform between diastolic and systolic phase can be observed. This is because the skull is expanded because of the intracranial pressuring during the systolic phase.

This shows that even when the speed of sound increases due to CSF vs. blood exchange for the particular region of interest for more than 8.75 m/s, the overall acoustic travel time of the package increases either because of the longer distance or the longer path. When subtracting $t_{sys}$ from $t_{dia}$, we receive the maximum difference of 94 ns shown in the following equation (Eqn. 13). The time-of-flight measurement has an adequate resolution which is more than ten times better than the expected range of approx. 94 ns (better than 90 ps).

$$t_{dia} - t_{sys} = |6.67556 \text{ } \mu s - 6.76953 \text{ } \mu s'| = 0.09396 \text{ } \mu s = 93.96 \text{ ns} \quad \text{(Eqn. 13)}$$

The maximum difference of 94 ns shown in equation (Eqn. 13) is the benchmark which is achieved with the method and device according to the disclosure. Thus, they are an adequate tool for supporting the medical diagnosis in the case of intracranial pressure and other pathologies for medical diagnostics. Time around ±45 ns should be measured with an adequate resolution, meaning better than 100 times (approx. 400 ps step) and faster than 30 measurements per second. Simultaneously, it must be noted that the time-of-flight difference (increase/decrease) can decrease when the skull expansion decreases, or even shift to the negative when the skull stops expanding because of the increased intracranial pressure. This can be very helpful information for urgent medical care.

EXAMPLE 2: DISPERSIVE ULTRASOUND AS A NON-INVASIVE DIAGNOSTIC SYSTEM

Acoustocerebrography (ACG) utilizes ultrasound quasi constant wave packages of different frequencies to interrogate a medium in order to provide propagation times for each of the transmitted frequencies. This method provides an estimation of the dispersion patterns c(f) for a specific contained medium. The observed propagation speed changes are usually very small and require a very precise measurement of the propagation speed. Instead of measuring the speed of sound in the mediums it is easier to accurately measure the propagation time of ultrasound signals.

By means of equation (Eqn. 4) shown above, the propagation speed c(f) can be estimated very precisely from the propagation time t(f) by assuming that the constant dimension d is known.

A very high sampling frequency is required for the received signal in order to accurately measure the propagation time t(f). To achieve the necessary accuracy, a sampling frequency in the GHz range (exactly 2.5 GHz at 400 ps resolution) is required. For the signal traveling from the transmitter to the receiver, it is thus necessary that the time resolution is in the range of sub-nanoseconds. Such a system would be very expensive and would have unacceptable power requirements for a portable device. Instead, it is known that an ultrasound signal can be described not only by its frequency, but also by the phase information, as shown in the following equation (Eqn. 14).

$$g(t) = S + A \sin(\omega t + \varphi) \quad \text{(Eqn. 14)}$$

Thus, the phase information of the ultrasound wave together with its amplitude must be used to overcome the requirement for a high sampling frequency in order to provide accurate estimations of propagation times. It is commonly known, that the phase information only covers a range from $-\pi$ to $+\pi$. Hence, it can only be used to obtain additional information about one period of the signal. Furthermore, this information keeps repeating itself. In this case, a phenomenon from wave theory is used, the beat-note. In acoustics, a beat is an interference pattern between two sounds of slightly different frequencies, perceived as a periodic variation in volume whose rate is the difference of the two frequencies. The beat-note is the result of the combination of two continuous wave signals which are close in pitch but not identical. The difference in frequency generates the beats. The frequency of the beat-note is given by the following equation (Eqn. 15).

$$f_{beat} = f_1 - f_2 \quad \text{(Eqn. 15)}$$

The closer $f_1$ and $f_2$ are, the lower the resulting frequency beat $f_{beat}$ and the longer the period of the resulting beat phase $T_{beat} = 1/f_{beat}$. Using this beat-note approach allows for the clear identification of a specific point in the signal. Once this unique point has been found, the phase information of the individual frequency can be used in specific situations to accurately calculate propagation times. In addition to the observed changes in propagation speed, different attenuation profiles can also be observed. The interdependence between wave speed and attenuation is in accordance with the Kramers-Kronig relation, where the relation shown in the following equation (Eqn. 16) is shown, inter alia.

$$\frac{1}{c_2} - \frac{1}{c_1} = -\frac{2}{\pi} * \int_{\omega_1}^{\omega_2} \frac{\alpha(\omega)}{\omega^2} d\omega \quad \text{(Eqn. 16)}$$

In the equation (Eqn. 16), $c_1$, $c_2$ are the propagation speeds (speed of sound) for waves with circular frequencies $\omega_1$ or $\omega_2$ and $\alpha(\omega)$ is the attenuation for waves with circular frequency $\omega$. After introducing $\omega = 2\pi f$, $\omega_1 = 2\pi * f_1$ and $\omega_2 = 2\pi * f_2$, the following equation (Eqn. 17) applies:

$$\frac{1}{c_2} - \frac{1}{c_1} = -\frac{1}{\pi^2} * \int_{\omega_1}^{\omega_2} \frac{\alpha(f)}{f^2} df \quad \text{(Eqn. 17)}$$

Such patterns of frequency-dependent attenuations and the corresponding propagation speeds can be used to identify the state of a medium or to track possible changes to the brain tissue in real time. To achieve the requested time resolution for a useful medical diagnostic picture (as shown in FIG. 5), some essential requirements for the phase determination must be met. In FIG. 5, the time-of-flight waveform heartbeat curve of a 72-year-old patient is shown; recorded with the ACG system as part of an authorized clinical study. The X-axis shows the time [t] in seconds (s) and the Y-axis shows the time-of-flight in microseconds (µs).

Assuming that the interesting acoustic measurement band for ACG is between 0.7 MHz and 2.7 MHz, this will set a following expectation for the signal phase resolution. We require a phase resolution better than 400 ps at a frequency of 0.7 MHz—higher frequencies provide a higher time resolution while the wavelength is shorter—this means that the time resolution will be greater. Assuming that the average speed of an acoustic quasi constant wave package in the skull is 1540 m/s, we can receive an explanation according to the equations listed above and the following equation (Eqn. 18).

$$\lambda = \frac{c}{f} = \frac{1540}{0.7e^6} = 2.2 \text{ mm} \quad \text{(Eqn. 18)}$$

As can be seen from equation (Eqn. 18), these 2.2 mm are the length of exactly one period (360° or $2\pi$ (Phase)) with the time duration of 1.4285714 µs. Consequently, the required phase resolution must be in the range of 0.1° or better.

EXAMPLE 3: EVALUATION OF THE TIME-OF-FLIGHT MEASUREMENT OF A PATIENT

When using ICP monitoring in clinical practice, it is very important to determine the validity of the obtained pressure value. Access to a high-resolution view of the intracranial pressure waveform thus offers a more accurate analysis of the obtained intracranial pressures. When carrying out the method according to the disclosure, it is thus important to verify whether the obtained ICP signal is truly representative of the intracranial pressure. In this manner, the person skilled in the art should ensure that there is in fact an oscillating pressure curve with the progressively decreasing P1, P2 and P3 notches present, which indicate the propagation of the cardiac pulse pressure signal. Such an oscillating pressure curve is shown in an exemplary manner in FIG. 6, in which the propagation of the cardiac pulse pressure signal, in particular an intracranial pressure measurement recorded by an intracranial pressure probe, is illustrated. The X-axis shows the time [t] in milliseconds (ms) and the Y-axis shows the intracranial pressure (ICP).

It is understood that deviations from the pressure curve illustrated as an example in FIG. 6 can indicate a changed intracranial compliance, a changed intracranial pressure, a disturbed cerebral blood flow and/or a pathological condition. For example, reversed P1 and P2 notches indicate a state of disturbed autoregulation.

A closer look at the waveform in FIG. 5 supports the conclusion of the above-stated example of use 1, as it shows a difference of approx. 50 ns in the time-of-flight measurement between the diastolic and the systolic phase. It also shows that the patient has a disturbed autoregulation, as the P1 and P2 notches are reversed, which can be seen in seconds 6, 7, 8, 9, 14, 15 and 16.

The invention claimed is:

1. A method for a noninvasive determination and/or monitoring of the intracranial compliance of a biological material, comprising the steps of:
    a) performing an acoustic spectroscopy of the biological material between a transmitting ultrasound probe and a receiving ultrasound probe, several acoustic transmitting signals of different frequencies being emitted into the biological material and corresponding reflected acoustic receiving signals of different frequencies being received after having passed through the biological material, and the biological material being a human or an animal skull; and
    b) comparing the acoustic transmitting signals with the corresponding acoustic receiving signals to determine time-of-flight values corresponding to changes in intercranial pressure dp; and
    c) determining an expansion of the biological material dV, a linear expansion and/or a volume expansion of the biological material being measured, and
    d) determining an intracranial compliance dV/dp of the biological material based on the comparison in step b) and the determination carried out in step c)
        wherein the acoustic spectroscopy is carried out in a direction of a frontal plane of a skull above an external ear canal in a position selected to transmit the signal along an acoustic measurement path through the right and left cerebrum, and the cerebrospinal fluid (CSF) and ventricles, the position further selected to maximize a probability that a full echo transmitted by the transmitting ultrasound is reflected from the opposite skull bone and received at the receiving ultrasound probe; and
        displaying the time of flight values and/or the intracranial compliance.

2. The method according to claim 1,
    wherein the method additionally comprises the steps of:
    determining a cerebral blood flow and/or a pathological condition of the biological material based on the intracranial compliance determined in step d).

3. The method according to claim 2, wherein the method additionally comprises the steps of:
    displaying the intracranial pressure, cerebral blood flow and/or pathological condition of the biological material.

4. The method according to claim 1, wherein the acoustic transmitting signals are emitted at a first position of the biological material and wherein the acoustic receiving signals are received at a second position of the biological material, and wherein the first and second position are identical or disposed opposite each other.

5. The method according to claim 1, wherein the acoustic spectroscopy is carried out in the area of a longitudinal cerebral fissure.

6. A device for a noninvasive determination and/or monitoring of the intracranial compliance of a biological material
    having a first means for performing an acoustic spectroscopy of the biological material, wherein the first means comprises an acoustic transmitting element for transmitting several acoustic transmitting signals of different frequencies and/or amplitudes into the biological material and an acoustic receiving element for receiving corresponding reflected and/or transmitted acoustic receiving signals of different frequencies and/or amplitudes after having passed through the biological material and wherein the biological material is a human or animal skull;
    having an evaluation unit for comparing the acoustic transmitting signals with the corresponding acoustic receiving signals to determine time-of-flight values;
    having a second means for determining an expansion of the biological material dV, wherein the second means comprises a measuring device for measuring a linear expansion and/or a volume expansion of the biological material; and
    having an analysis unit configured to determine an intracranial compliance dV/dp of the biological material
    wherein the acoustic spectroscopy and/or the determination of the expansion of the biological material are carried out in a direction of the frontal plane of a human or animal skull above an external ear canal in a position selected to transmit the signal through the right and left cerebrum, the cerebrospinal fluid (CSF), and ventricles, the position further selected to maximize the probability that a full echo transmitted by the transmitting ultrasound is reflected from the opposite skull bone and received at the receiving ultrasound probe; and
        displaying the time-of flight values and/or the intracranial compliance.

7. The device according to claim 6, wherein the analysis unit is configured to determine an intracranial pressure, a cerebral blood flow and/or a pathological condition of the biological material based on an intracranial compliance determined by the analysis unit.

8. The device according to claim 6, further comprising an output unit for displaying a determination carried out by means of the analysis unit.

9. The device according to claim 6, wherein the acoustic transmitting element is disposed at a first position of the biological material and wherein the acoustic receiving element is disposed at a second position of the biological material and wherein the first and the second position are identical or disposed opposite each other.

10. The device according to claim 6, wherein the acoustic spectroscopy and/or the determination of the expansion of the biological material are carried out in the area of a left and a right cerebrum and a longitudinal cerebral fissure.

11. The device according to claim 6, wherein the first means, the second means, the evaluation unit, the analysis unit and/or the output unit are disposed in one component.

12. The device according to claim 6, wherein the device is realized so as to be rotatable and/or moveable.

13. A method for a noninvasive determination and/or monitoring of the intracranial pressure of a human or an animal skull, comprising the steps of:
- a) performing an acoustic spectroscopy of the biological material between a transmitting ultrasound probe and a receiving ultrasound probe, several acoustic transmitting signals of different frequencies being emitted into the biological material and corresponding reflected acoustic receiving signals of different frequencies being received after having passed through the biological material, wherein the acoustic spectroscopy is carried out in a direction of a frontal plane of a skull above an external ear canal in a position selected to transmit the signal along an acoustic measurement path through the right and left cerebrum, and the cerebrospinal fluid (CSF) and ventricles, the position further selected to maximize a probability that a full echo transmitted by the transmitting ultrasound is reflected from the opposite skull bone and is received at the receiving ultrasound probe;
- b) comparing the acoustic transmitting signals with the corresponding acoustic receiving signals to determine time-of-flight values corresponding to changes in intercranial pressure; and
- c) displaying the time of flight values that correspond to the intracranial pressure to monitor the intracranial pressure.

* * * * *

UNITED STATES PATENT AND TRADEMARK OFFICE
CERTIFICATE OF CORRECTION

PATENT NO. : 12,318,242 B2
APPLICATION NO. : 17/599182
DATED : June 3, 2025
INVENTOR(S) : Miroslaw Wrobel It is certified that error appears in the above-identified patent and that said Letters Patent is hereby corrected as shown below:

In the Specification

Column 14, Line 5, "d" should be --$d_i$--.

Column 16, Line 60, "µs'=0.09396" should be --$\mu s| = 0.09396$--.

Column 18, Line 50, "2π(Phase)" should be --2π Phase)--.

Signed and Sealed this
Fifth Day of August, 2025

Coke Morgan Stewart
*Acting Director of the United States Patent and Trademark Office*